United States Patent
Ren et al.

(10) Patent No.: US 11,297,788 B2
(45) Date of Patent: Apr. 12, 2022

(54) ECHINACEA CULTIVAR 'BALSOMPOCEL'

(71) Applicant: Ball Horticultural Company, West Chicago, IL (US)

(72) Inventors: Jianping Ren, Geneva, IL (US); Robert B. Eisenreich, North Aurora, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/934,772

(22) Filed: Jul. 21, 2020

(65) Prior Publication Data

US 2021/0000045 A1    Jan. 7, 2021

(51) Int. Cl.
*A01H 6/14* (2018.01)
*A01H 5/02* (2018.01)

(52) U.S. Cl.
CPC ............. *A01H 6/1448* (2018.05); *A01H 5/02* (2013.01); *A01H 6/14* (2018.05)

(58) Field of Classification Search
CPC .................................................... A01H 6/1448
See application file for complete search history.

(56) References Cited

U.S. PATENT DOCUMENTS

PP28,769 P2 * 12/2017 Korlipara ................. A01H 6/14 Plt./428
PP30,116 P2    1/2019 Ren

OTHER PUBLICATIONS

Abbasi, et al., "Echinacea biotechnology: Challenges and opportunities," Plant, 43:481-492, 2007.
Ault, "Coneflower, Echinacea species," p. 799-822. In: Flower Breeding and Genetics: Issues, Challenges, and Opportunities for the 21st Century, Anderson, N. O., ed., The Netherlands, Springer, 2006.
Koroch et al., "In vitro regeneration of Echinacea purpurea from leaf explants." Plant Cell, Tissue, and Organ Culture, 69:79-83, 2002.
Mcgregor et al., "The Taxonomy of the Genus Echinacea," Univ. Of Kansas Science Bulletin, 48(4):113-142, 1968.
Parsons, et al., "Echinacea biotechnology: advances, commercialization and future considerations," Pharm. Biol., 56 (1): 485-494, 2018.
Rice, "A New Dawn for Echinacea," Plantsman, 212-219, 2007.

* cited by examiner

*Primary Examiner* — David H Kruse
(74) *Attorney, Agent, or Firm* — Dentons US LLP

(57) ABSTRACT

The invention provides plants of the *Echinacea* cultivar designated 'Balsompocel'. The invention thus relates to the plants, cells, plant parts, and tissue cultures of the cultivar 'Balsompocel', and to methods for producing an *Echinacea* plant produced by crossing an *Echinacea* plant of cultivar 'Balsompocel' with another *Echinacea* plant, such as a plant of another cultivar. The invention further relates to *Echinacea* seeds and plants produced by crossing plants of cultivar 'Balsompocel' with plants of another cultivar. The invention further relates to the genetic complements and hybrid genetic complements of plants of cultivar 'Balsompocel'.

26 Claims, 2 Drawing Sheets
(2 of 2 Drawing Sheet(s) Filed in Color)

ECHINACEA CULTIVAR 'BALSOMPOCEL'

BACKGROUND OF THE INVENTION

Field of the Invention

The present invention relates to the field of plant breeding and, more specifically, to *Echinacea* plants having a flower that comprises a non-fading color trait. In particular, the invention relates to plants of the cultivar designated 'Balsompocel', and derivatives and tissue cultures thereof.

Description of Related Art

*Echinacea*, commonly known as coneflower, is a member of the Asteraceae family. The genus *Echinacea* is composed of eleven taxa, nine North American indigenous species and two varieties. See, for example, McGregor et al. (*Univ. Of Kansas Science Bulletin*, 48(4):113-142, 1968; specifically incorporated herein by reference it is entirety).

*Echinacea* has a rich tradition of medicinal use by North American Plains Indians. Currently, three of the species, *E. angustifolia*, *E. pallida*, and *E. purpurea*, have commercial value as herbal remedies for providing general immune-boosting effects. These species along with *E. paradoxa* and *E. tennesseensis* have ornamental value as popular landscape plants and cut flowers.

*Echinacea* are herbaceous perennial plants having a basal rosette of leaves and erect flowering stems. The flower heads have many fertile disc florets borne on a flattened to raised receptacle, and typically have a single outer whorl of sterile ray florets. The flower heads have a bristly appearance due to the stiff, sharp palea subtending the disc florets. As a garden perennial, *E. purpurea* is the most common species, and has flower colors that range from purple through pink shades to white. Hybridization with yellow flowered *E. paradoxa* has broadened the color range. See, for example, Rice (*Plantsman*, 212-219, 2007; specifically incorporated herein by reference it is entirety).

*Echinacea* can be propagated from seed or tissue culture or by division. "Division" as used herein refers to an asexual plant propagation method wherein a plant is separated into two or more parts with each part having an intact root and crown. Seed germination protocols for several of the species are well-known in the art. See, for example, Ault (Coneflower, *Echinacea* species, p. 799-822. In: Flower Breeding and Genetics: Issues, Challenges, and Opportunities for the 21st Century, Anderson, N. O., ed., The Netherlands, Springer, 2006; specifically incorporated herein by reference it is entirety).

Although, *Echinacea* species hybridize easily and many fertile $F_1$ hybrids can be produced, *Echinacea* breeding has barriers. Historically, the genus was described as being completely self-incompatible, however a later study of *E. angustifolia* reported up to 9% self-pollinations. While the degree and type of self-incompatibility remains unknown, breeding strategies employing mass selection or phenotypic recurrent selection offer models for the development and maintenance of *Echinacea* seed lines. See, for example, Ault (Coneflower, *Echinacea* species, p. 799-822. In: Flower Breeding and Genetics: Issues, Challenges, and Opportunities for the 21st Century, Anderson, N. O., ed., The Netherlands, Springer, 2006

SUMMARY OF THE INVENTION

In one aspect, the invention provides an *Echinacea* plant of cultivar 'Balsompocel'. Also provided are seeds and plants having all of the physiological and morphological characteristics of such plants. Parts of these *Echinacea* plants are also provided, for example, including a stem, a leaf, an axillary bud, a disc floret, a ray floret, pollen, or an ovule.

In another aspect of the invention, a tissue culture of regenerable cells of *Echinacea* cultivar 'Balsompocel' is provided. The tissue culture will preferably be capable of regenerating *Echinacea* plants capable of expressing all of the physiological and morphological characteristics of the starting plant and of regenerating plants having substantially the same genotype as the starting plant. Examples of some of the physiological and morphological characteristics of *Echinacea* cultivar 'Balsompocel' include those traits set forth in the phenotypic description provided herein. The regenerable cells in such tissue culture may be derived, for example, from a stem, a leaf, an axillary bud, a disc floret, a ray floret, pollen, or an ovule. Still further, the present invention provides *Echinacea* plants regenerated from a tissue culture of the invention, the plants having all of the physiological and morphological characteristics of *Echinacea* cultivar 'Balsompocel'.

In another yet another aspect, the invention provides a method of vegetatively propagating an *Echinacea* plant comprising the steps of: (a) collecting tissue capable of being propagated from a plant of *Echinacea* cultivar 'Balsompocel'; and (b) propagating a plant from said tissue. The method will preferably be capable of producing *Echinacea* plants capable of expressing all of the physiological and morphological characteristics of the starting plant and of producing plants having substantially the same genotype as the starting plant. Still further, the present invention provides *Echinacea* plants produced by vegetative propagation of *Echinacea* cultivar 'Balsompocel'. In some embodiments, such plants have all of the physiological and morphological characteristics of *Echinacea* cultivar 'Balsompocel'.

In one aspect, a plant of *Echinacea* cultivar 'Balsompocel' further comprising an added heritable trait is provided. In some embodiments, the heritable trait may comprise a transgene or may comprise a genetic locus that is, for example, a dominant or recessive allele. In specific embodiments, the added genetic locus may confer one or more traits, such as for example, herbicide tolerance, pest resistance, or disease resistance, or a ray floret color selected from the group consisting of yellow, yellow-orange, orange, coral, salmon, pink, rose, red, red-orange, scarlet, red-purple, purple, burgundy, and blue-violet. In further embodiments, the trait may be conferred by a naturally occurring gene introduced into the genome of a line by backcrossing, a non-transgenic mutation, or a transgene introduced through genetic transformation techniques into the plant or a progenitor of any previous generation thereof. When introduced through transformation, a genetic locus may comprise one or more genes integrated at a single chromosomal location.

In another aspect, a plant of *Echinacea* cultivar 'Balsompocel' further comprising a single locus conversion is provided. In some embodiments, a single locus conversion includes one or more site-specific changes to the plant genome, such as, without limitation, one or more nucleotide modifications, deletions, or insertions. A single locus may comprise one or more genes or nucleotides integrated or mutated at a single chromosomal location. In one embodiment, a single locus conversion may be introduced by a genetic engineering technique, methods of which include, for example, genome editing with engineered nucleases (GEEN). Engineered nucleases include, but are not limited to, Cas endonucleases; zinc finger nucleases (ZFNs); transcription activator-like effector nucleases (TALENs); engineered meganucleases, also known as homing endonucleases; and other endonucleases for DNA or RNA-guided genome editing that are well-known to the skilled artisan. The single locus conversion may confer one or more traits, such as for example, a ray floret color selected from the group consisting of yellow, yellow-orange, orange, coral, salmon, pink, rose, red, red-orange, scarlet, red-purple, purple, burgundy, and blue-violet.

In yet another aspect, the invention provides a method comprising applying plant breeding techniques to a plant of *Echinacea* cultivar 'Balsompocel'. In some embodiments, the method comprises producing an *Echinacea* cultivar 'Balsompocel'-derived *Echinacea* plant. Non-limiting examples of plant breeding techniques include recurrent selection, mass selection, hybridization, open-pollination, backcrossing, modified backcrossing, pedigree breeding, mutation breeding, or marker assisted selection. In one embodiment, the method comprises selecting an *Echinacea* cultivar 'Balsompocel'-derived *Echinacea* plant that comprises the non-fading flower color trait found in *Echinacea* cultivar 'Balsompocel'. In specific embodiments, an *Echinacea* plant produced by the breeding techniques described herein may have a ray floret color selected from the group consisting of yellow, yellow-orange, orange, coral, salmon, pink, rose, red, red-orange, scarlet, red-purple, purple, burgundy, and blue-violet. In one embodiment, an *Echinacea* plant produced by the breeding techniques described herein may have at least one semi-double or double flower type inflorescence.

In still yet another aspect, the present invention provides a method of obtaining an *Echinacea* plant with a non-fading flower color trait comprising producing a progeny plant of *Echinacea* cultivar 'Balsompocel'. In some embodiments, the method comprises: (a) crossing a plant of cultivar 'Balsompocel' with a plant of a second *Echinacea* cultivar to produce $F_1$ progeny; (b) selecting an $F_1$ progeny that comprises a non-fading flower color trait comprised in the plant of cultivar 'Balsompocel'; (c) backcrossing the selected $F_1$ progeny with a plant of the same cultivar as said second *Echinacea* cultivar; and (d) repeating steps (b) and (c) one or more times to produce a selected backcrossed progeny that comprises the non-fading flower color trait. In one embodiment, progeny plants of *Echinacea* cultivar 'Balsompocel' are provided. Such plants, for example, may comprise a non-fading flower color trait found in *Echinacea* cultivar 'Balsompocel'.

In one aspect, the present invention provides a method of introducing a trait into an *Echinacea* plant, the method comprising the steps of: (a) crossing a plant of cultivar 'Balsompocel' with a second *Echinacea* plant that comprises the trait to produce $F_1$ progeny; (b) selecting an $F_1$ progeny that comprises the trait; (c) backcrossing the selected $F_1$ progeny with a plant of cultivar 'Balsompocel' to produce backcross progeny; and (d) repeating steps (b) and (c) three or more times to produce a selected fourth or higher backcross progeny that comprises the trait. In some embodiments, plants produced by such methods are also provided.

In another aspect, the present invention provides a method comprising vegetatively propagating an *Echinacea* plant comprising a non-fading color trait, wherein the plant is the product of applying a plant breeding technique to a plant of *Echinacea* cultivar 'Balsompocel'.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features, and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Definitions

Figure 1:
FIG. 1: Illustrates the overall growth and flowering habit of *Echinacea* plants of the cultivar designated 'Balsompocel'.
Figure 2:
FIG. 2: Illustrates a close-up view of an individual inflorescence of *Echinacea* plants of the cultivar designated 'Balsompocel'.

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first generation hybrid ($F_1$) with one of the parental genotypes of the $F_1$ hybrid.

Crossing: The pollination of a female flower of an *Echinacea* plant, thereby resulting in the production of seed from the flower.

Cross-pollination: Fertilization by the union of two gametes from different plants.

Diploid: A cell or organism having two sets of chromosomes.

$F_1$ Hybrid: The first generation progeny of the cross of two plants.

Genetic Complement: An aggregate of nucleotide sequences, the expression of which sequences defines the phenotype in *Echinacea* plants, or components of plants including cells or tissue.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Non-transgenic mutation: A mutation that is naturally occurring (spontaneous), or induced by conventional methods (e.g. exposure of plants to radiation or mutagenic compounds), not including mutations made using recombinant DNA techniques.

Phenotype: The detectable characteristics of a cell or organism in which the characteristics are the manifestation of gene expression.

Quantitative Trait Loci (QTL): Genetic loci that contribute, at least in part, certain numerically representable traits that are usually continuously distributed.

Regeneration: The development of a plant from tissue culture.

SSR profile: A profile of simple sequence repeats used as genetic markers and scored by gel electrophoresis following PCR amplification using flanking oligonucleotide primers.

Self-pollination: The transfer of pollen from the anther to the stigma of the same plant.

Single Locus Converted (Conversion) Plant: Plants that are developed by a plant breeding technique called backcrossing or by genetic engineering of a locus, wherein essentially all of the morphological and physiological characteristics of a plant are recovered in addition to the characteristics conferred by the single locus transferred into the plant via the backcrossing or genetic engineering technique.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic sequence that has been introduced into the nuclear or chloroplast genome of an *Echinacea* plant by genetic transformation or site-specific modification.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

*Echinacea* Cultivar 'Balsompocel'

The disclosure provides *Echinacea* plants with dark yellow ray florets that comprise a non-fading color trait, wherein said non-fading color trait is defined as comprising a ray floret that exhibits reduced fading during senescence as compared to a ray floret having the same hue from other known *Echinacea* cultivars.

A. Origin and Breeding History

*Echinacea* cultivar 'Balsompocel' was selected as a single flowering plant from the cross of proprietary *Echinacea* x *hybrida* breeding selection E97-6-12-D and proprietary *Echinacea* x *hybrida* breeding selection E100-2-2-2. During trials, plants of the selected cultivar were surprisingly observed to comprise a non-fading color trait. The dark yellow ray florets of the selected cultivar exhibited markedly reduced fading during senescence compared to all other known yellow-colored *Echinacea* cultivars. In addition, the selected cultivar produced a short, highly basally branched plant. This combination of traits is unique compared to all other known *Echinacea* cultivars. The selected plant was coded ECH-308 and later given the cultivar name 'Balsompocel'.

The female parent, *Echinacea* x *hybrida* breeding selection E97-6-12-D, is characterized by its single-type, medium yellow-colored ray florets, medium green-colored foliage, and moderately vigorous, semi-upright growth habit. The male parent, *Echinacea* x *hybrida* breeding selection E100-2-2-2, is characterized by its single-type, medium bright yellow-colored ray florets, medium green-colored foliage, and moderately vigorous, semi-upright growth habit. *Echinacea* cultivar 'Balsompocel' has a darker yellow ray floret color and a more compact growth habit compared to either of its parents.

Asexual reproduction of *Echinacea* cultivar 'Balsompocel' by in vitro shoot propagation since September 2015 has demonstrated that *Echinacea* cultivar 'Balsompocel' reproduces true-to-type for all of the physiological and morphological characteristics described herein. All of the physiological and morphological characteristics described herein are firmly fixed and retained through successive generations of such asexual propagation.

B. Phenotypic Description

In accordance with another aspect of the present invention, there is provided an *Echinacea* plant having the morphological characteristics of *Echinacea* cultivar 'Balsompocel'. A description of the morphological and physiological characteristics of *Echinacea* plant 'Balsompocel' is presented below.

The following characteristics have been repeatedly observed and can be used to distinguish 'Balsompocel' as a new and distinct cultivar of *Echinacea* plant:

1. Single-type, dark yellow-colored inflorescences;
2. Medium green-colored foliage; and
3. Moderately vigorous, compact-upright growth habit.

'Balsompocel' has not been observed under all possible environmental conditions. Phenotype may vary due to environmental influence without variation in genotype. *Echinacea* cultivar 'Balsompocel' shows uniformity and stability within the limits of environmental influence for the traits described herein. No variant traits have been observed or are expected in 'Balsompocel'.

Color ratings were determined using the RHS Colour Chart of The Royal Horticultural Society of London (RHS), 2015 Edition, except where general color terms of ordinary significance are used. Color ratings were determined in August 2019 under natural light conditions in Elburn, Ill. The following describe approximately eight-month-old plants produced from in vitro plantlets under conditions comparable to those used in commercial practice. Measurements and numerical values represent averages of typical plants. *These are typical values. Values may vary due to environment. Other values that are substantially equivalent are within the scope of the invention.

Botanical classification: *Echinacea* x *hybrida* 'Balsompocel'.

Parentage:
Female parent.—Proprietary *Echinacea* x *hybrida* breeding selection coded E97-6-12-D, not patented.
Male parent.—Proprietary *Echinacea* x *hybrida* breeding selection coded E100-2-2-2, not patented.

Propagation:
Type.—In vitro propagation is preferred, divisions are possible.
Time to initiate roots in vitro.—Approximately 2 weeks at 24° C.
Time to produce a rooted plantlet.—Approximately 4 weeks at 24° C.
Root description.—Fine, fibrous; grey to light brown in color.
Rooting habit.—Moderate density, moderate branching.

Plant Description:
Commercial crop time.—Approximately 10 to 12 weeks from a rooted tissue culture plantlet to finish in a 15 cm container.
Growth habit and general appearance.—Herbaceous perennial, moderately vigorous, compact-upright.
Hardiness.—USDA Zone 5a (−20° F. to −15° F./−28.9° C. to −26° C.).
Size.—Height from soil level to top of plant plane: Approximately 34.0 cm. Width: Approximately 43.0 cm.
Branching habit.—No lateral branching, flowering stems grow from base. Quantity of main stems per plant: Approximately 9.
Stems.—Strength: Very strong. Aspect: Nearly erect. Shape: Rounded. Length to base of inflorescence: Approximately 29.0 cm. Diameter: Approximately 5.0 mm to 8.0 mm. Length of central internode: Approximately 3.0 cm. Texture: Densely pubescent with short strigose hairs. Color of young and mature stems: 146D to 145A.

Foliage Description:
General description.—Form: Simple. Arrangement: Alternate.
Leaves.—Aspect: Perpendicular to stem, subtending with age. Shape: Narrowly ovate to lanceolate. Margin: Entire to shallowly serrate, slightly undulate. Apex: Acute. Base: Attenuate. Venation pattern: Pinnate. Length of mature leaf: Approximately 13.0 cm. Width of mature leaf: Approximately 4.0 cm. Texture of upper surface: Dull, moderately pubescent with short strigose hairs. Texture of lower surface: Moderately pubescent with short strigose hairs. Color of upper surface of young and mature foliage: Closest to NN137A with venation of 145C. Color of lower surface of young and mature foliage: Closest to 147B with venation of 145C.
Petiole.—Shape: V-shaped. Length: Approximately 3.5 cm to 5.5 cm. Diameter: Approximately 3.0 mm to 6.0 mm. Texture of upper surface: Glabrous. Texture of lower surface: Sparsely covered with very short strigose hairs. Color of upper and lower surfaces: 145B to 145C.

Flowering Description:
Flowering habit.—'Balsompocel' is freely flowering blooming from late spring through late summer under outdoor growing conditions.
Lastingness of individual inflorescence on the plant.—Approximately 3 weeks.

Inflorescence Description:
General description.—Type: Single, composite. Persistent. Shape: Conical. Aspect: Facing upward. Arrangement: Terminal, held upright on strong peduncles. Fragrance: Faintly sweet. Quantity per plant: Approximately 10. Height: Approximately 4.0 cm. Diameter: Approximately 9.0 cm.
Peduncle.—Strength: Strong. Aspect: Erect to approximately 45° from vertical. Length: Approximately 9.5 cm. Diameter: Approximately 5.0 mm. Texture: Densely pubescent with short strigose hairs. Color: 146D to 145A.
Bud.—Quantity per plant: Approximately 6. Shape: Flattened globular with immature ray florets nearly erect. Length: Approximately 1.5 cm. Diameter: Approximately 1.8 cm. Color: Outer ray florets of 8C with bud center of 143A.
Ray florets.—Quantity per inflorescence: Approximately 23. Arrangement: In a single whorl, imbricate. Aspect: Perpendicular to disc, subtending slightly with age. Shape: Elliptic. Appearance: Dull. Margin: Entire. Apex: Emarginate to notched. Base: Attenuate. Length: Approximately 4.0 cm. Width: Approximately 1.3 cm. Texture of upper surface: Glabrous, ribbed longitudinally. Texture of lower surface: Sparsely pubescent, ribbed longitudinally. Color of upper surface when first open: Darker than but closest to 15A tinted with 137C at base. Color of lower surface when first open: 12D. Color of upper surface when fully open: 15A tinted with 137C at base, with senescence transitions to 15C. Color of lower surface when fully open: 11D, with senescence transitions to 11C tinted with 137C.
Disc florets.—Disc diameter: Approximately 4.0 cm. Quantity per inflorescence: Approximately 260. Arrangement: Spirally arranged in center of inflorescence. Shape: Tubular. Margin of free portion: Entire. Apex: Five acute tips. Base: Fused into a tube. Length: Approximately 1.2 cm. Diameter: Approximately 2.0 mm. Texture: Glabrous. Color of upper or inner surface when first and fully open: 144B. Color of lower or outer surface when first and fully open: 144B with base of NN155D.
Receptacle.—Shape: Conical. Height: Approximately 1.1 cm. Diameter: Approximately 1.3 cm. Color: 155D.
Phyllaries.—Quantity per inflorescence Approximately 60. Arrangement: In multiple whorls. Appearance: Dull, stiff. Shape: Narrowly ovate to lanceolate, strongly curved towards the peduncle. Margin: Entire, ciliate. Apex: Acute. Base: Truncate. Length: Approximately 9.0 mm to 1.5 cm. Width: Approximately 2.0 mm to 3.0 mm. Texture of upper or inner surface: Glabrous. Texture of lower or outer surface: Sparsely pubescent with short strigose hairs. Color of upper surface: 137A. Color of lower surface: 137B.
Receptacle spines.—Number of spines per disc: Approximately 260. Shape: Acicular. Length: Approximately 1.3 cm. Width at widest point: Approximately 2.0 mm. Apex: Acute. Base: Truncate. Texture: Glabrous. Color: Apex of 23A with a small spot of 187A at tip, midsection of 144A, and base of NN155D.
Reproductive organs.—Androecium: Present on disc florets only. Stamen quantity: 5 per floret. Anther shape: Oblong, basifixed. Anther length: Approximately 3.0 mm. Anther color: Closest to 200A. Filament length: Approximately 3.0 mm. Filament color: NN155D. Pollen amount: Abundant. Pollen color: 13A. Gynoecium: Present on disc florets only. Pistil quantity: 1 per floret. Pistil length: Approximately 1.2 cm. Stigma shape: Bifid. Stigma length: Approximately 2.0 mm. Stigma color: 145D. Style length: Approximately 7.0 mm.

Style color: 145D. Ovary length: Approximately 3.0 mm. Ovary color: NN155D.

C. Deposit Information

A deposit of representative sample of plant tissue of *Echinacea* cultivar 'Balsompocel' was made with the Provasoli-Guillard National Center for Marine Algae and Microbiota (NCMA), 60 Bigelow Drive, East Boothbay, Me., 04544 USA. The deposit was assigned NCMA Accession No. 202001001. The date of deposit of the representative sample of plant tissue with the NCMA was Jan. 7, 2020. The deposit has been accepted under the Budapest Treaty and will be maintained in the NCMA depository for a period of 30 years, or 5 years after the most recent request, or for the enforceable life of the patent, whichever is longer, and will be replaced if necessary during that period. Upon issuance, all restrictions on the availability to the public of the deposit will be irrevocably removed consistent with all of the requirements of the Budapest Treaty and 37 C.F.R. §§ 1.801-1.809. Applicant does not waive any infringement of rights granted under this patent or under the Plant Variety Protection Act (7 USC 2321 et seq.).

Further Embodiments of the Invention

A. Plant Breeding

In one aspect, the present disclosure provides plants modified using the methods described herein to include at least a first desired heritable trait. Such plants may, in one embodiment, be developed by backcrossing, wherein essentially all of the desired morphological and physiological characteristics of a cultivar are recovered in addition to a genetic locus transferred into the plant via the backcrossing technique. The term single locus converted plant as used herein refers to those plants which are developed by backcrossing or by genetic engineering, wherein essentially all of the desired morphological and physiological characteristics of a cultivar are recovered in addition to the single locus transferred into the cultivar via the backcrossing or genetic engineering technique, respectively. By essentially all of the desired morphological and physiological characteristics, it is meant that the characteristics of a plant are recovered that are otherwise present when compared in the same environment, other than an occasional variant trait that might arise during backcrossing, direct introduction of a transgene, or application of genetic engineering technique.

Backcrossing methods can be used with the present invention to improve or introduce a trait into a cultivar. The term backcrossing as used herein refers to the repeated crossing of a hybrid progeny back to one of the parental *Echinacea* plants. The parental *Echinacea* plant that contributes the locus or loci for the desired trait is termed the nonrecurrent or donor parent. This terminology refers to the fact that the nonrecurrent parent is used one time in the backcross protocol and therefore does not recur. The recurrent parent therefore provides the desired genetic background, while the choice of the particular nonrecurrent parent will depend on the purpose of the backcross. One of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele or an additive allele (between recessive and dominant) may also be transferred. In this instance it may be necessary to introduce a test of the progeny to determine if the desired characteristic has been successfully transferred. The backcross process may be accelerated by the use of genetic markers, such as SSR, RFLP, SNP or AFLP markers to identify plants with the greatest genetic complement from the recurrent parent.

Modified backcrossing may also be used with plants comprising a non-fading color trait. This technique uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (*Plant Physiol.*, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, herbicide tolerance, disease resistance, pest resistance, and ray floret color. These genes are generally inherited through the nucleus, but may be inherited through the cytoplasm.

Selection of *Echinacea* plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming, or otherwise disadvantageous. In addition, marker assisted selection may be used to identify plants comprising desirable genotypes at the seed, seedling, or plant stage, to identify or assess the purity of a cultivar, to catalog the genetic diversity of a germplasm collection, and to monitor specific alleles or haplotypes within an established cultivar.

Types of genetic markers which could be used in accordance with the invention include, but are not necessarily limited to, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

In particular embodiments of the invention, marker assisted selection is used to increase the efficiency of a backcrossing breeding scheme for producing an *Echinacea* line comprising a desired trait. This technique is commonly referred to as marker assisted backcrossing (MABC). This technique is well-known in the art and may involve, for example, the use of three or more levels of selection, including foreground selection to identity the presence of a desired locus, which may complement or replace phenotype screening protocols; recombinant selection to minimize linkage drag; and background selection to maximize recurrent parent genome recovery.

B. Breeding of *Echinacea* Cultivar 'Balsompocel'

The development of new varieties using one or more starting varieties is well known in the art and encompassed by the disclosure. In accordance with the disclosure, novel varieties may be created by crossing a plant of the disclosure followed by multiple generations of breeding according to such well-known methods. New varieties may be created by crossing with any second plant. New varieties may be developed, for example, by applying a breeding technique to a plant of *Echinacea* cultivar 'Balsompocel'. Such breeding techniques are well-known in the art and include but are not limited to recurrent selection, mass selection, hybridization, open-pollination, backcrossing, modified backcrossing, pedigree breeding, mutation breeding, and marker assisted selection. "Mutation breeding" as used herein refers to a breeding technique comprising selecting a naturally occurring (spontaneous) mutation or inducing a mutation through means such as irradiation or chemical induction. *Echinacea* plants produced by applying breeding techniques to a plant of *Echinacea* cultivar 'Balsompocel' may for example have a ray floret color that is different from that of *Echinacea* cultivar 'Balsompocel'. Non-limiting examples of ray floret colors that may be produced by applying breeding techniques to a plant of *Echinacea* cultivar 'Balsompocel' include yellow, yellow-orange, orange, coral, salmon, pink, rose, red, red-orange, scarlet, red-purple, purple, burgundy, and blue-violet.

In selecting a second plant to cross with a plant of the disclosure, it will typically be preferred to choose those plants which either themselves exhibit one or more selected desirable characteristics or which exhibit the desired characteristic(s) when in hybrid combination. Once initial crosses have been made, selection takes place to produce new varieties. Examples of desirable traits may include, in specific embodiments, flower color or size, color patterning, foliage quality, floret size, shape and uniformity, maturity date, flower yield, seed germination rate, seedling vigor, pest and disease resistance, herbicide tolerance, and adaptability for soil and climate conditions. Consumer-driven traits are other traits that may be incorporated into new plants developed by this disclosure.

One aspect of the current disclosure therefore provides methods for producing an *Echinacea* plant comprising a flower that exhibits a non-fading color trait. In certain embodiments, the method may comprise (a) producing an *Echinacea* cultivar 'Balsompocel'-derived *Echinacea* plant from a seed produced by crossing a plant of *Echinacea* cultivar 'Balsompocel' with itself or a second *Echinacea* plant; (b) crossing the *Echinacea* cultivar 'Balsompocel'-derived *Echinacea* plant with itself or a different *Echinacea* plant to obtain a seed of a further *Echinacea* cultivar 'Balsompocel'-derived *Echinacea* plant; (c) selecting a further *Echinacea* cultivar 'Balsompocel'-derived *Echinacea* plant that comprises the non-fading color trait; (d) repeating said producing, crossing, and selecting steps of (a), (b), and (c) using the seed of said step (b) for at least one generation to produce a seed an additional 'Balsompocel'-derived *Echinacea* plant; and (e) selecting an additional *Echinacea* cultivar 'Balsompocel'-derived *Echinacea* plant that comprising the non-fading color trait. In a particular embodiment, the second plant may be an *Echinacea* plant and the progeny seed may be planted and grown to produce fertile hybrid progeny plants. A plant in accordance with the disclosure may be used in such crosses as the female plant or the male plant.

The disclosure also provides methods of producing *Echinacea* plants derived from *Echinacea* cultivar 'Balsompocel'. The method may comprise (a) crossing an *Echinacea* plant of *Echinacea* cultivar 'Balsompocel' with itself or a second plant capable of being crossed thereto; and (b) collecting resulting seed. In one embodiment, the second plant may be an *Echinacea* plant. In some embodiments, the methods of the present disclosure may further comprise the step of (c) crossing a plant grown from said seed of step (b) with itself or a second plant at least one or more additional time(s) to yield additional seed. Plants, seeds, and plant parts produced from the methods described herein and plants comprising the non-fading color trait as described herein are also provided.

In certain embodiments, hybrid seeds may be produced using the methods of the present disclosure. A parent plant of such a seed may be an *Echinacea* plant of *Echinacea* cultivar 'Balsompocel'. In other embodiments, a plant as described herein may be either the male plant or the female plant in a given cross.

In accordance with the disclosure, any species of *Echinacea* may be used. In particular, *Echinacea* species that may be useful include but are not limited to *Echinacea angustifolia, Echinacea atrorubens, Echinacea laevigata, Echinacea pallida, Echinacea paradoxa, Echinacea purpurea, Echinacea sanguinea, Echinacea serotina, Echinacea simulata, Echinacea tennesseensis*, and the like.

C. Plants Derived by Genetic Engineering

Various genetic engineering technologies have been developed and may be used by those of skill in the art to introduce traits in plants. In certain aspects of the claimed invention, traits are introduced into *Echinacea* plants via altering or introducing a single genetic locus or transgene into the genome of a recited variety or progenitor thereof. Methods of genetic engineering to modify, delete, or insert genes and polynucleotides into the genomic DNA of plants are well-known in the art.

In specific embodiments of the invention, improved *Echinacea* cultivars can be created through the site-specific modification of a plant genome. Methods of genetic engineering include, for example, utilizing sequence-specific nucleases such as zinc-finger nucleases (see, for example, U.S. Pat. Appl. Pub. No. 2011-0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359 and 8,771,945 and U.S. Pat. Appl. Pub. No. 2014-0068797). One embodiment of the invention thus relates to utilizing a nuclease or any associated protein to carry out genome modification. This nuclease could be provided heterologously within donor template DNA for templated-genomic editing or in a separate molecule or vector. A recombinant DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in an *Echinacea* plant genome (see, for example Sauer et al., *Plant Physiol*, 170(4):1917-1928, 2016).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment of the invention, genetic transformation may be used to insert a selected transgene into a plant of the disclosure or may, alternatively, be used for the preparation of transgenes which can be introduced by backcrossing. Methods for the transformation of plants that are well known to those of skill in the art and applicable to many plant species include, but are not limited to, electroporation, microprojectile bombardment, *Agrobacterium*-mediated transformation and direct DNA uptake by protoplasts. For example, Wang, et al., describes *Agrobacterium*-mediated transformation of *Echinacea* (*Colloids and Surfaces B: Biointerfaces*, 53(1):101-104, 2006).

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (U.S. Pat. No. 5,563,055, incorporated herein by reference in its entirety). Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest and disease resistance, and any other gene of agronomic interest. Examples of constitutive promoters useful for driving gene expression in plants include, but are not limited to, the cauliflower mosaic virus (CaMV) P-35S promoter, which confers constitutive, high-level expression in most plant tissues, including monocots; a tandemly duplicated version of the CaMV 35S promoter, the enhanced 35S promoter (P-e35S) the nopaline synthase promoter, the octopine synthase promoter; and the figwort mosaic virus (P-FMV) promoter as described in U.S. Pat. No. 5,378,619 (incorporated herein by reference in its entirety), and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter; maize rbcS promoter; or chlorophyll a/b-binding protein promoter), (3) hormones, such as abscisic acid, (4) wounding (e.g., wun1); or (5) chemicals such as methyl jasmonate, salicylic acid, or Safener. It may also be advantageous to employ organ-specific promoters.

Exemplary nucleic acids which may be introduced to the plants of this disclosure include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of Echinacea cultivar 'Balsompocel'. Non-limiting examples of particular genes and corresponding phenotypes one may choose to introduce into a of the disclosure include one or more genes for insect tolerance, such as a Bacillus thuringiensis (B.t.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a Bacillus insect control protein gene as described in WO 99/31248, U.S. Pat. Nos. 5,689,052, 5,500,365 and 5,880,275, each of which are herein incorporated by reference in their entirety. In another embodiment, the structural gene can confer tolerance to the herbicide glyphosate as conferred by genes including, but not limited to Agrobacterium strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or co-suppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present disclosure.

D. Genetic Complements

In another aspect of the invention, the genetic complement of the Echinacea plant cultivar designated 'Balsompocel' is provided. The phrase "genetic complement" is used to refer to the aggregate of nucleotide sequences, the expression of which sequences defines the phenotype of, in the present case, an Echinacea plant, or a cell or tissue of that plant. A genetic complement thus represents the genetic makeup of cell, tissue or plant, and a hybrid genetic complement represents the genetic makeup of a hybrid cell, tissue or plant. The invention thus provides Echinacea plant cells that have a genetic complement in accordance with the Echinacea plant cells disclosed herein, and plants, seeds and diploid plants containing such cells.

Plant genetic complements may be assessed by genetic marker profiles, and by the expression of phenotypic traits that are characteristic of the expression of the genetic complement, e.g., isozyme typing profiles. It is understood that cultivar 'Balsompocel' could be identified by any of the many well-known techniques such as, for example, Simple Sequence Length Polymorphisms (SSLPs) (Williams et al., Nucleic Acids Res., 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., Science, 280:1077-1082, 1998).

In yet another aspect, the present invention provides hybrid genetic complements, as represented by Echinacea plant cells, tissues, plants, and seeds, formed by the combination of a haploid genetic complement of an Echinacea plant of the invention with a haploid genetic complement of the same or a different cultivar. In another aspect, the present invention provides an Echinacea plant regenerated from a tissue culture that comprises a hybrid genetic complement of this invention.

E. Additional Traits

Additional traits can be introduced into the Echinacea cultivar of the present invention. A non-limiting example of such a trait is a coding sequence that decreases RNA and/or protein levels. The decreased RNA and/or protein levels may be achieved through RNAi methods, such as those described in U.S. Pat. No. 6,506,559 to Fire and Mellow.

Another trait that may find use with the Echinacea cultivar of the invention is a sequence that allows for site-specific recombination. Examples of such sequences include the FRT sequence, used with the FLP recombinase (Zhu and Sadowski, J. Biol. Chem., 270:23044-23054, 1995); and the LOX sequence, used with CRE recombinase (Sauer, Mol. Cell. Biol., 7:2087-2096, 1987). The recombinase genes can be encoded at any location within the genome of the Echinacea plant, and are active in the hemizygous state.

It may also be desirable to make Echinacea plants more tolerant to or more easily transformed with Agrobacterium tumefaciens. Expression of p53 and iap, two baculovirus cell-death suppressor genes, inhibited tissue necrosis and DNA cleavage. Additional targets can include plant-encoded proteins that interact with the Agrobacterium Vir genes; enzymes involved in plant cell wall formation; and histones, histone acetyltransferases and histone deacetylases (reviewed in Gelvin, Microbiology & Mol. Biol. Reviews, 67:16-37, 2003).

F. Plants Comprising Non-Transgenic Mutations

In still yet another aspect, a plant of Echinacea cultivar designated 'Balsompocel', further comprising a non-transgenic mutation is provided. The phrase "non-transgenic mutation" is used herein to refer to a mutation that is naturally occurring (spontaneous), or induced by conventional methods (e.g. exposure of plants to radiation or mutagenic compounds), not including mutations made using recombinant DNA techniques. Various mutagenesis techniques have been developed and may be used by those of skill in the art to induce mutations in plants. Methods of mutagenesis may include, for example, exposure to irradiation, mutagenic compounds, extreme heat, or tissue culture conditions; long-term seed storage; and targeting induced local lesions in genomes (TILLING). In some embodiments, ionizing radiation may be produced by X-rays, gamma rays, neutrons, beta rays, or ultraviolet rays. Non-limiting examples of chemical mutagens include base analogues, antibiotics, alkylating agents, sodium azide, hydroxylamine, nitrous acid, methylnitrilsourea, and acridines. Methods of mutagenesis to modify, delete, or insert polynucleotides into the genomic DNA are well-known in the art.

In one aspect, improved *Echinacea* cultivars may be created through mutation of the plant genome. In one embodiment, a plant of the *Echinacea* cultivar 'Balsompocel' may be subjected to a mutagenesis technique to create a population of mutant plants. Such mutant plants, for example, may comprise a mutation and otherwise comprise all of the physiological and morphological characteristics of *Echinacea* cultivar 'Balsompocel'. In particular embodiments, mutant plants may comprise a mutation and otherwise comprise all of the morphological and physiological characteristics of *Echinacea* cultivar 'Balsompocel' with the exception of flower color or plant height. Mutant plants of *Echinacea* cultivar 'Balsompocel' may, for example, have ray floret colors including, but not limited to, shades of yellow, yellow-orange, orange, coral, salmon, pink, rose, red, red-orange, scarlet, red-purple, purple, burgundy, and blue-violet. Mutant plants of *Echinacea* cultivar 'Balsompocel' may be shorter than or taller than wild-type 'Balsompocel'. Shorter mutant plants of *Echinacea* cultivar 'Balsompocel' may be suitable for pot plant use, while taller mutant plants of *Echinacea* cultivar 'Balsompocel' may be suitable for landscape plantings or cut flower use.

G. Tissue Cultures and In Vitro Regeneration of *Echinacea* Plants

In another aspect, the invention relates to tissue cultures of the *Echinacea* plant designated 'Balsompocel'. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, meristems, cotyledons, pollen, leaves, anthers, roots, root tips, pistil, flower, florets, seed, stems, and the like. In a preferred embodiment, the tissue culture comprises cells derived from immature tissues of these plant parts. Means for preparing and maintaining plant tissue cultures are well known in the art (Abbasi, et al., *In Vitro Cell Dev. Biol.-Plant*, 43:481-492, 2007, and Parsons, et al., *Pharm. Biol.*, 56(1): 485-494, 2018, each incorporated herein by reference in their entirety).

In yet another aspect, compositions are provided comprising a cell of *Echinacea* cultivar 'Balsompocel' comprised in plant cell growth media. Plant cell growth media are well known to those of skill in the art. For example, Koroch, et al., describes plant regeneration via organogenesis from callus cultures derived from leaf tissue of *Echinacea purpurea* (*Plant Cell, Tissue, and Organ Culture*, 69: 79-83, 2002; specifically incorporated herein by reference). Plant cell growth media can provide adequate support for plant cells, including providing moisture and/or nutritional components.

H. Processes of Crossing *Echinacea* Plants and the *Echinacea* Plants Produced by Such Crosses The present invention provides processes of preparing novel *Echinacea* plants and *Echinacea* plants produced by such processes. In accordance with such a process, a first parent *Echinacea* plant may be crossed with a second parent *Echinacea* plant wherein at least one of the first and second *Echinacea* plants is the *Echinacea* plant 'Balsompocel'. One application of the process is in the production of $F_1$ hybrid plants. Another important aspect of this process is that it can be used for the development of novel cultivars. For example, the *Echinacea* plant 'Balsompocel' could be crossed to any second plant, and the resulting hybrid progeny could be vegetatively propagated or the hybrid progeny could be each selfed for about 5 to 7 or more generations, thereby providing a large number of distinct cultivars. These cultivars could then be crossed with other cultivars and the resulting hybrid progeny analyzed for beneficial characteristics. In this way, novel cultivars conferring desirable characteristics could be identified. "Vegetative propagation" as used herein refers to any form of asexual reproduction occurring in plants in which a new plant grows from a fragment of the parent plant. Non-limiting examples of vegetative propagation methods include tissue culture and division.

I. $F_1$ Hybrid *Echinacea* Plant and Seed Production

One beneficial use of the instant *Echinacea* cultivar is in the production of hybrid seed. Any time the *Echinacea* plant 'Balsompocel' is crossed with another, different, *Echinacea* plant, a first generation ($F_1$) *Echinacea* hybrid plant is produced. As such, an $F_1$ hybrid *Echinacea* plant can be produced by crossing 'Balsompocel' with any second *Echinacea* plant. Essentially any other *Echinacea* plant can be used to produce a hybrid *Echinacea* plant having *Echinacea* plant 'Balsompocel' as one parent. All that is required is that the second plant be fertile, which *Echinacea* plants naturally are, and that the plant is not *Echinacea* cultivar 'Balsompocel'.

The goal of the process of producing an $F_1$ hybrid is to manipulate the genetic complement of *Echinacea* to generate new combinations of genes that interact to yield new or improved traits (phenotypic characteristics).

*Echinacea* has a diploid phase, which means two conditions of a gene (two alleles) occupy each locus (position on a chromosome). If the alleles are the same at a locus, there is said to be homozygosity. If they are different, there is said to be heterozygosity.

Hundreds of *Echinacea* varieties are known to those of skill in the art, any one of which could be crossed with *Echinacea* plant 'Balsompocel' to produce a hybrid plant. For example, the U.S. Patent & Trademark Office has issued more than 200 plant patents for *Echinacea* varieties.

When the *Echinacea* plant 'Balsompocel' is crossed with another *Echinacea* plant to yield a hybrid, it can serve as either the maternal or paternal plant. For many crosses, the outcome is the same regardless of the assigned sex of the parental plants. Depending on the seed production characteristics relative to a second parent in a hybrid cross, it may be desired to use one of the parental plants as the male or female parent. Seed coat characteristics can be preferable in one plant. Pollen can be shed better by one plant. Therefore, a decision to use one parent plant as a male or female may be made based on any such characteristics as is well known to those of skill in the art.

J. Development of *Echinacea* Varieties

The development of new varieties using one or more starting varieties is well known in the art. In accordance with the invention, novel varieties may be created by crossing

*Echinacea* cultivar 'Balsompocel' followed by vegetative propagation of selected plants. In certain embodiments, novel varieties may be created by crossing *Echinacea* cultivar 'Balsompocel' followed by multiple generations of breeding according to such well-known methods. New varieties may be created by crossing *Echinacea* cultivar 'Balsompocel' with any second plant. In selecting such a second plant to cross for the purpose of developing novel varieties, it may be desired to choose those plants that either themselves exhibit one or more selected desirable characteristics or exhibit the desired characteristic(s) when in hybrid combination. Examples of potentially desired characteristics include flower color or size, color patterning, foliage quality, floret size, shape and uniformity, maturity date, flower yield, seed germination rate, seedling vigor, pest and disease resistance, and adaptability for soil and climate conditions.

Once initial crosses have been made with *Echinacea* cultivar 'Balsompocel', vegetative propagation or inbreeding takes place to produce new varieties. Inbreeding requires manipulation by human breeders. Even in the extremely unlikely event inbreeding rather than crossbreeding occurred in natural *Echinacea*, achievement of complete inbreeding cannot be expected in nature due to well-known deleterious effects of homozygosity and the large number of generations the plant would have to breed in isolation. The reason for the breeder to create inbred plants is to have a known reservoir of genes whose gametic transmission is predictable.

The pedigree breeding method involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and selected in successive generations. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. After at least five generations, the inbred plant is considered genetically pure.

Uniform lines of new varieties may also be developed by way of double-haploids. This technique allows the creation of true breeding lines without the need for multiple generations of selfing and selection. In this manner true breeding lines can be produced in as little as one generation. Haploid induction systems have been developed for various plants to produce haploid tissues, plants and seeds. The haploid induction system can produce haploid plants from any genotype by crossing with an inducer line. Inducer lines and methods for obtaining haploid plants are known in the art.

EXAMPLES

Example 1—Distinguishing Characteristics of *Echinacea* Cultivar 'Balsompocel'

The most similar, commercially available *Echinacea* cultivar to 'Balsompocel' is the *Echinacea* cultivar designated 'Balsomemyim' (U.S. PP30,116). However, 'Balsompocel' can be distinguished from 'Balsomemyim' by at least the following characteristics: 1) 'Balsompocel' has a fully open ray floret color that is a darker shade of yellow compared to the fully open ray floret color of 'Balsomemyim'; 2) 'Balsompocel' has more basal branches per plant compared to 'Balsomemyim'; 3) 'Balsompocel' has a ray floret color that transitions from 15A to 15C during senescence, thus maintaining a darker shade of yellow compared to 'Balsomemyim', which transitions from 12A to 12B then to 4D during senescence. Fading ray floret color as shown for 'Balsomemyim' is typical for all known commercial *Echinacea* cultivars.

Example 2—Hybrid Plants Produced from *Echinacea* Cultivar 'Balsompocel'

The present invention provides $F_1$ hybrid *Echinacea* plants derived from the *Echinacea* plant 'Balsompocel'. Table 1 illustrates that 'Balsompocel', coded ECH-308, was used as a parent in a number of hybrid crosses, and that hybrid seeds were recovered from all crosses shown. The hybrid code in Table 1 identifies a lot of hybrid seeds rather than individual hybrid plants. Methods for producing *Echinacea* plants from *Echinacea* seeds are well known in the art.

TABLE 1

Hybrid Plants Having 'Balsompocel' as One Parent

| Hybrid code | Female code | Female ray floret color | Male code | Male ray floret color | No. seeds produced |
|---|---|---|---|---|---|
| Ech601-F | Ech208 | red | ECH-308 | yellow | 166 |
| Ech601-R | ECH-308 | yellow | Ech208 | red | 210 |
| Ech605-F | Ech288-1 | purple | ECH-308 | yellow | 229 |
| Ech605-R | ECH-308 | yellow | Ech288-1 | purple | 285 |
| Ech606-2019 | ECH-308 | yellow | Ech291-1-1 | red | 286 |
| Ech606-F | Ech291 | red (dark cone) | ECH-308 | yellow | 115 |
| Ech606-R | ECH-308 | yellow | Ech291 | red (dark cone) | 108 |
| Ech624 | Ech-289-1 | yellow golden | ECH-308 | yellow | 63 |
| Ech624-R | Ech289-2 | yellow | ECH-308 | yellow | 24 |
| Ech643 | E97-6-8-1-2-1 | yellow | ECH-308 | yellow | 3 |
| Ech674 | E114-3-3-1-1-1 | purple | ECH-308 | yellow | 45 |
| Ech706-R | Ech272 | yellow | ECH-308 | yellow | 52 |
| Ech707 | ECH-308 | yellow | Ech286-2-3 | yellow | 6 |
| Ech733-F | Ech264 | burgundy | ECH-308 | yellow | 6 |
| Ech734-F | Ech268-1 | orange | ECH-308 | yellow | 39 |
| Ech757-F | Ech277 | orange-purple-burgundy | ECH-308 | yellow | 544 |
| Ech757-R | ECH-308 | yellow | Ech277 | orange-purple-burgundy | 100 |

TABLE 1-continued

Hybrid Plants Having 'Balsompocel' as One Parent

| Hybrid code | Female code | Female ray floret color | Male code | Male ray floret color | No. seeds produced |
|---|---|---|---|---|---|
| Ech766-F | Ech290 | dark purple | ECH-308 | yellow | 50 |
| Ech775-F | Ech296-1 | purple | ECH-308 | yellow | 64 |
| Ech777-F | Ech219-14-1 | yellow light | ECH-308 | yellow | 10 |
| Ech777-R | ECH-308 | yellow | Ech219-14-1 | light yellow | 127 |
| Ech904 | Ech286-2-2 | yellow | ECH-308 | yellow | 25 |
| Ech909 | Ech231-14-2-2 | golden orange | ECH-308 | yellow | 369 |
| Ech911 | Ech256-14-2-2 | orange | ECH-308 | yellow | 122 |

Example 3—*Echinacea* Plants with Double Type and Semi-Double Type Inflorescences Produced from *Echinacea* Cultivar 'Balsompocel'

*Echinacea* cultivar 'Balsompocel', code ECH-308, was used in developmental crosses with three double flower type, female *Echinacea* plants with the goal of obtaining 'Balsompocel'-derived *Echinacea* plants with double flower type inflorescences (Table 2). Due to the limited number of ECH-308 plants available, pollen from a range of yellow, single flower type plants was mixed with ECH-308 pollen. It is well-known in the art that the cross of a homozygous, double flower type *Echinacea* plant and a single flower type *Echinacea* plant produces double flower type progeny. Likewise, it is well known it the art that the cross of a heterozygous, double flower type *Echinacea* plant and a single flower type *Echinacea* plant produces double flower type, semi-double flower type, and single flower type progeny.

TABLE 2

*Echinacea* Plants with Double Type and Semi-Double Type Inflorescences Having 'Balsompocel' as One Parent

| Female code - Double flower type | Female ray floret color | Male code - Single flower type | Male ray floret color | No. seeds produced |
|---|---|---|---|---|
| ECH279 | creamy yellow | Ech266, Ech270, Ech272, Ech276, Ech280, Ech286, ECH-308 | shades of yellow | 26 |
| ECH301 | orange | Ech266, Ech270, Ech272, Ech276, Ech280, Ech286, ECH-308 | shades of yellow | 50 |
| ECH318 | orange | Ech266, Ech270, Ech272, Ech276, Ech280, Ech286, ECH-308 | shades of yellow | 48 |

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The references cited herein, to the extent that they provide exemplary procedural or other details supplementary to those set forth herein, are specifically incorporated herein by reference.

What is claimed is:

1. An *Echinacea* plant of cultivar 'Balsompocel', a representative sample of plant tissue of said cultivar having been deposited under NCMA Accession No. 202001001.

2. A seed of the plant of claim 1.

3. A plant part of the plant of claim 1, wherein said plant part comprises at least one cell of said plant.

4. The plant part of claim 3, defined as a stem, leaf, axillary bud, disc floret, ray floret, pollen, or ovule.

5. An *Echinacea* plant having all of the physiological and morphological characteristics of the plant of claim 1.

6. A tissue culture of regenerable cells of the plant of claim 1.

7. An *Echinacea* plant regenerated from the tissue culture of claim 6.

8. A method of vegetatively propagating an *Echinacea* plant comprising the steps of:
   (a) collecting tissue capable of being propagated from the plant of claim 1; and
   (b) propagating a plant from said tissue.

9. An *Echinacea* plant produced by the method of claim 8.

10. A method of producing an *Echinacea* plant comprising an added trait, the method comprising introducing a transgene conferring the trait into the plant of claim 1.

11. An *Echinacea* plant produced by the method of claim 10.

12. An *Echinacea* plant of cultivar 'Balsompocel', a representative sample of plant tissue of said cultivar having been deposited under NCMA Accession No. 202001001, further comprising a transgene.

13. An *Echinacea* plant of cultivar 'Balsompocel', a representative sample of plant tissue of said cultivar having been deposited under NCMA Accession No. 202001001, further comprising a single locus conversion, wherein said single locus conversion is introduced into the cultivar 'Balsompocel' by genetic engineering, spontaneous mutation, or induced mutation, and wherein said plant comprises the single locus conversion and otherwise comprises all of the physiological and morphological characteristics of *Echinacea* cultivar 'Balsompocel'.

14. The plant of claim 13, wherein said single locus conversion comprises a non-transgenic mutation.

15. The plant of claim 14, wherein the non-transgenic mutation confers a ray floret color selected from the group consisting of yellow, yellow-orange, orange, coral, salmon, pink, rose, red, red-orange, scarlet, red-purple, purple, burgundy, and blue-violet.

16. A method of plant breeding comprising applying a plant breeding technique to the plant according to claim 1.

17. The method of claim 16, defined as comprising producing an *Echinacea* cultivar 'Balsompocel'-derived *Echinacea* plant.

18. The method of claim 16, wherein said plant breeding technique comprises recurrent selection, mass selection, hybridization, open-pollination, backcrossing, modified backcrossing, pedigree breeding, mutation breeding, or marker assisted selection.

19. The method of claim 17, further defined as comprising selecting an *Echinacea* cultivar 'Balsompocel'-derived *Echinacea* plant that comprises a non-fading flower color trait found in said *Echinacea* cultivar 'Balsompocel'.

20. A first generation *Echinacea* cultivar 'Balsompocel'-derived *Echinacea* plant produced by the method of claim 17, wherein said plant comprises the non-fading flower color trait and has a ray floret color selected from the group consisting of yellow, yellow-orange, orange, coral, salmon, pink, rose, red, red-orange, scarlet, red-purple, purple, burgundy, and blue-violet.

21. A first generation *Echinacea* cultivar 'Balsompocel'-derived *Echinacea* plant produced by the method of claim 17, wherein said plant comprises the non-fading flower color trait and has at least one semi-double or double flower type inflorescence.

22. A method of obtaining an *Echinacea* plant with a non-fading flower color trait comprising producing a progeny plant of a plant according to claim 1.

23. The method of claim 22, further defined as comprising:
(a) crossing the plant of cultivar 'Balsompocel' with a plant of a second *Echinacea* cultivar to produce a progeny plant;
(b) selecting a progeny plant that comprises a non-fading flower color trait comprised in the plant of cultivar 'Balsompocel';
(c) backcrossing the selected progeny plant with a plant of the same cultivar as said second *Echinacea* cultivar; and
(d) repeating steps (b) and (c) one or more times to produce a further selected progeny that comprises the non-fading flower color trait.

24. A method of producing a cultivar Balsompocel'-derived *Echinacea* plant, the method comprising crossing the plant of cultivar 'Balsompocel' according to claim 1 with a second *Echinacea* plant.

25. A plant produced by the method of claim 24, wherein said plant is a first generation cultivar 'Balsompocel'-derived *Echinacea* plant, and wherein said plant comprises a non-fading flower color trait comprised in the plant of cultivar 'Balsompocel'.

26. A method for producing an *Echinacea* plant comprising a non-fading color trait, said method comprising vegetatively propagating an *Echinacea* plant comprising the non-fading color trait, wherein said plant is the product of applying a plant breeding technique to the plant of claim 1.

\* \* \* \* \*